United States Patent
Andolino Brandt et al.

(10) Patent No.: US 6,958,154 B2
(45) Date of Patent: *Oct. 25, 2005

(54) SPRAY ON BANDAGE AND DRUG DELIVERY SYSTEM

(75) Inventors: Patricia J. Andolino Brandt, Woodbury, MN (US); Charles M. Leir, Falcon Heights, MN (US); David J. Wirtanen, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/619,008

(22) Filed: Jul. 14, 2003

(65) Prior Publication Data

US 2004/0013629 A1 Jan. 22, 2004

Related U.S. Application Data

(63) Continuation of application No. 09/784,385, filed on Feb. 15, 2001, now Pat. No. 6,627,216, which is a continuation of application No. 09/136,903, filed on Aug. 20, 1998, now abandoned.

(51) Int. Cl.⁷ ............................................. A61K 9/00
(52) U.S. Cl. ................... 424/400; 424/443; 424/449
(58) Field of Search ............................. 424/400, 443, 424/449

(56) References Cited

U.S. PATENT DOCUMENTS

| | | | |
|---|---|---|---|
| RE24,906 E | 12/1960 | Ulrich | |
| 4,737,577 A | 4/1988 | Brown | |
| 4,751,087 A | 6/1988 | Wick | |
| 4,814,168 A | 3/1989 | Sablotsky et al. | |
| 4,861,764 A | 8/1989 | Samour et al. | |
| 5,082,866 A | 1/1992 | Wong et al. | |
| 5,103,812 A * | 4/1992 | Salamone et al. | 602/52 |
| 5,196,410 A | 3/1993 | Francoeur et al. | |
| 5,214,119 A | 5/1993 | Leihr et al. | |
| 5,290,615 A | 3/1994 | Tushaus et al. | |
| 5,300,291 A | 4/1994 | Sablotsky et al. | |
| 5,461,134 A | 10/1995 | Leir et al. | |
| 5,474,783 A | 12/1995 | Miranda et al. | |
| 5,512,650 A | 4/1996 | Leir et al. | |
| 5,656,286 A | 8/1997 | Miranda et al. | |
| 5,670,598 A | 9/1997 | Leir et al. | |
| 5,686,099 A | 11/1997 | Sablotsky et al. | |
| 5,750,630 A | 5/1998 | Sengupta | |
| 6,627,216 B2 * | 9/2003 | Wirtanen et al. | 424/443 |

FOREIGN PATENT DOCUMENTS

| | | |
|---|---|---|
| DE | 19654468 C1 | 1/1998 |
| EP | 0 290 262 | 11/1988 |
| EP | 0 390 541 B2 | 10/1990 |
| EP | 0 319 555 B1 * | 1/1992 |
| EP | 0 713 708 A1 | 5/1996 |
| WO | WO 96/34029 | 10/1996 |
| WO | WO 97/01327 | 1/1997 |
| WO | WO 97/15295 | 5/1997 |
| WO | WO 97/29735 | 8/1997 |
| WO | WO 98/23291 | 4/1998 |
| WO | WO 99/63955 | 12/1999 |
| ZA | 96/2536 | 3/1996 |

* cited by examiner

Primary Examiner—Shelley A. Dodson
Assistant Examiner—Konata M. George
(74) Attorney, Agent, or Firm—Sean J. Edmond; Cheree'Haswell Johnson

(57) ABSTRACT

The present invention provides novel "patch in a bottle" technology in which a fluid composition, e.g., an aerosol spray, is applied onto a surface as a fluid, but then dries to form a covering element, such as a patch, having a tack free outer surface covering an underlying adhesive that helps adhere the patch to the substrate. The fluid compositions have a unique chemical formulation that allows such composite patches to form in situ. Specifically, the fluid compositions include a tacky component, such as an adhesive, and a film-forming, non-tacky component. The non-tacky and tacky components are selected to be immiscible with each other so that the components undergo phase separation as the fluid composition dries.

12 Claims, No Drawings

SPRAY ON BANDAGE AND DRUG DELIVERY SYSTEM

CROSS REFERENCE TO RELATED APPLICATIONS

This application is a continuation of U.S. Ser. No. 09/784,385, filed Feb. 15, 2001, now U.S. Pat. No. 6,627,216, which, in turn, is a continuation of U.S. Ser. No. 09/136,903, filed Aug. 20, 1998, now abandoned, the disclosure of which is herein incorporated by reference.

FIELD OF THE INVENTION

This invention is in the field of compositions and related methods for forming covering elements suitable for use as a patch for transtissue delivery (e.g., transdermal delivery, delivery by absorption through oral tissues or other mucosal membranes, or the like) of therapeutic agents and/or for use as a bandage for covering wounds. More specifically, this invention relates to fluid compositions that are coated onto a surface of a host animal and then dried to form, in situ, a covering element, such as a transdermal patch, bandage, or the like, having a touch-dry, non-tacky outer surface, and a tacky inner surface for adhering the covering element to the host. Depending upon the application, pharmacologically active agents and/or penetration enhancers may be incorporated into the compositions.

BACKGROUND OF THE INVENTION

Transtissue drug delivery is a non-invasive therapeutic method in which a drug is first placed onto a tissue of a host animal and then caused to penetrate into the tissue in furtherance of the desired therapeutic treatment. Transtissue drug delivery can be used to treat topical, local, or systemic medical conditions. Delivery can occur across a number of different tissues including the skin, mucosal membranes, oral tissue, or the like. Delivery through the skin is generally referred to as "transdermal" drug delivery.

Transdermal drug delivery is typically accomplished by using a covering element in the form of a transdermal patch device that is attached to the host at the desired drug delivery site. A typical transdermal patch structure includes a drug-in-adhesive layer sandwiched between an impermeable backing and a release liner. At the time of use, the release liner is easily removed so that the patch can be attached to the host, adhesive side down. The impermeable backing thus traps the drug-in-adhesive layer between the backing and the attachment site of the host. Over time, the drug penetrates into the host, or is topically active, in accordance with the desired therapeutic treatment. Optionally, the drug-in-adhesive formulation may include one or more compounds known as penetration enhancers that increase the delivery of the drug to the subject.

Although the peel and place type of transdermal drug delivery device has been an extremely effective means to accomplish drug delivery for a wide variety of medical conditions, there are still a number of ways in which transdermal drug delivery, and transtissue drug delivery in general, could be improved. For instance, the structure of the conventional peel and place patch currently involves a manufacturing operation requiring the drug-in-adhesive to be coated onto a substrate, e.g., the impermeable backing or the release liner, as the case may be. This kind of coating step involves substantial expense in terms of capital equipment, utilities, manufacturing space, and human resources needed to carry out the coating operation. To avoid such expense, it would be desirable to design an alternative, or to eliminate entirely the need for such a coating step.

Furthermore, the use of a release liner creates an item of waste in the sense that the release liner must be discarded in some fashion after being removed from the patch. It would be desirable to provide a more environmentally-friendly alternative, or to avoid this kind of waste entirely.

Transtissue drug delivery could further be improved if customized patches were to be made whose drug concentration or rate of delivery was custom tailored to the needs of individual patients. Currently, it is not economically feasible to do this, because patches of a particular drug formulation are typically made in large numbers using mass production techniques. Consequently, patch manufacturers typically formulate transtissue delivery patches to be generally efficacious for the population as a whole. Of course, this approach has been and will continue to be effective in many instances, but some situations exist in which a treatment could be optimized, and patient suffering further alleviated, by a customized patch formulation.

Furthermore, transtissue drug delivery would be improved if the rate of drug delivery could be more effectively controlled. That is, initially, when the concentration of the drug in the patch is still relatively high, current patches generally deliver the drug at a relatively high rate. However, as the concentration of the drug in the patch is depleted, the rate of drug delivery generally slows down. Thus, the efficiency of current patches generally and undesirably varies over time. A patch that is characterized by a steady, consistent rate of drug delivery over a longer period of time would provide a more optimal treatment option in some instances.

Finally, currently available transtissue delivery systems are not particularly "user-friendly." That is, the application of a transdermal patch requires many steps; unwrapping of the patch, peeling away of the release liner and disposal of the release liner and wrapper. Additionally, some of the larger-sized conventional patches may be uncomfortable to wear since they may not conform easily to the contour of the body. As a result, movement of the area where the patch is located may cause discomfort.

SUMMARY OF THE INVENTION

The present invention provides a novel "patch in a bottle" technology. More specifically, the present invention provides a fluid composition, e.g., an aerosol spray in some embodiments, that is applied onto a surface as a fluid, but subsequently dries to form a covering element, such as a patch, on a surface of a host. The covering element so formed has a tack free outer surface covering and an underlying tacky surface that helps adhere the patch to the substrate.

The fluid compositions of the present invention have a unique chemical formulation that allows a covering element to form in situ. Specifically, the fluid compositions include a tacky component, such as an adhesive, and a film-forming, non-tacky component. The non-tacky and tacky components are selected to be immiscible with each other so that the components undergo phase separation once the fluid compositions are applied to the surface of a host and subsequently dried. The non-tacky component has characteristics that cause it to seek the surface of the coated fluid composition, where it dries to form a non-tacky, protective film. The tacky component dries below this film, providing the bottom surface of the covering element with sufficient tack to adhere to the surface of a host.

One or more pharmacologically active agents are easily incorporated into the fluid compositions, so that the corresponding covering elements can be used for transtissue drug delivery, e.g., transdermal drug delivery, delivery through a mucosal membrane, or the like. The present invention offers numerous advantages for transtissue drug delivery. Firstly, in as much as the fluid compositions of the present invention may be easily prepared with varied concentrations of pharmacologically active agents, it is both economically feasible and time efficient to customize the fluid compositions such that patient treatment is optimized. In fact, specific fluid compositions containing concentrations of a drug custom-tailored to the specific needs of individual patients can be specially formulated at a health facility, pharmacy, or the like, rather than at a manufacturing facility. As a result, the medical professional is provided with more treatment options and thus, tremendous flexibility to treat patients on an individualized basis.

As an additional advantage, the fluid compositions of the present invention may be formulated to provide a predetermined, desired rate of drug delivery. Specifically, and as mentioned above, the tacky and non-tacky components of the fluid compositions undergo phase separation upon drying, resulting in the covering element so formed having one or more discrete tacky domains. These tacky domains provide a diffusion path by which a pharmacologically active agent, or drug, may diffuse from the tacky phase to the surface of the host. The rate of drug delivery from the covering element can thus be varied by varying the amount of tacky component in the fluid composition from which the covering element is formed. For example, the rate of drug delivery from the covering element can be increased by increasing the amount of the tacky component in the fluid composition. Analogously, the rate of drug delivery can be decreased by decreasing the amount of the tacky component in the fluid composition. Alternatively, the fluid compositions may be formulated to provide a predetermined, desired rate of drug delivery simply by increasing or decreasing the amount of drug in the fluid composition to produce a corresponding increase or decrease, respectively, in the rate of drug delivery from the corresponding covering element. These two rate controlling approaches can be used in combination, if desired.

The fluid compositions of the present invention may also advantageously be formulated so that the corresponding covering elements provide a more controlled, consistent and sustained rate of delivery of the drug as compared to the conventional peel and place patches. Some conventional patches tend to provide a very high initial drug delivery rate that tends to decrease logarithmically relatively soon, i.e., only a few hours, after placement on the patient. In contrast, covering elements in accordance with some embodiments of the present invention are believed to provide steady, constant rates of drug delivery over extended periods of time, e.g., 20 to 50 hours or more.

The fluid compositions of the present invention also provide many advantages to the end-user. Particularly, the fluid compositions of the present invention may be easily applied in one step, e.g., as by spraying, onto the desired surface. The corresponding covering element forms in situ, without the need for further effort on the part of the end-user. In contrast, conventional peel and place patches generally require that the end-user remove any outer wrapping, peel off the release liner, and then apply the patch to the skin.

Additionally, inasmuch as the covering element is formed in situ and applied as a fluid, the covering element of the present invention is capable of conforming to a surface of various sizes or shapes. Because the covering element is so flexible, it is relatively comfortable to wear. Conventional peel and place patches, on the other hand, come in preformed shapes and sizes and thus may have difficulty adhering and/or conforming to some surfaces. The patches may also be less comfortable for the wearer.

Finally, the fluid compositions of the present invention provide many manufacturing and/or environmental benefits. For example, the manufacture of a conventional patch involves the step of coating a drug-in-adhesive onto a substrate, a step which involves substantial expense. The fluid compositions of the present invention do not require such a coating step. Conventional patches also typically include a release liner to cover the adhesive surface until the patch is to be used, at which time the release liner must be discarded, creating undesirable waste. In contrast, the use of a release liner is completely avoided when using the fluid compositions of the present invention.

Thus, in one aspect, the present invention provides a fluid composition suitable for in situ forming and adhering a covering element onto a surface. The composition includes an effective amount of a tacky component such that the formed covering element adheres to the surface and a film-forming, non-tacky component, wherein the film-forming, non-tacky component comprises at least one low surface energy, surface-seeking moiety. Additionally, the film-forming, non-tacky component is immiscible with the tacky component and is present in an effective amount such that an outer surface of the in situ formed covering element is non-tacky when the covering element is dried. The composition also includes a sufficient amount of at least one volatile solvent such that the fluid composition has a coatable viscosity allowing the fluid composition to be coated onto the surface.

In another aspect, the present invention relates to a fluid composition suitable for in situ forming and adhering a touch-dry, non-tacky covering element onto a surface of a host. The composition includes a pressure sensitive adhesive (PSA) component and a siloxane containing polymer. The PSA component is present in an effective amount such that the covering element adheres to the host surface. The siloxane containing polymer is present in an effective amount such that an outer surface of the in situ formed covering element is non-tacky when the covering element is touch dry. The composition also includes a sufficient amount of at least one volatile solvent such that the fluid composition has a coatable viscosity allowing the fluid composition to be coated onto the host surface. As used herein, "siloxane containing polymer" refers to a polymer whose backbone comprises a plurality of siloxane units, which may be linked to each other in the form of polysiloxane units.

In another aspect the present invention relates to a covering element, comprising first and second opposed major surfaces. A first, tacky phase is precipitately formed proximal to the first surface such that the first surface is sufficiently tacky to allow the covering element to be adhered to a surface of a host. A second, non-tacky, film phase is precipitately formed proximal to the second surface so that the second surface is non-tacky. The film phase comprises at least one low surface energy, surface seeking moiety.

In another aspect, the present invention relates to a transdermal drug delivery system, comprising first and second opposed major surfaces. A first, tacky phase is precipitately formed proximal to the first surface such that the first surface is sufficiently tacky to allow the transdermal drug delivery system to be adhered to a surface of a host. A second, non-tacky, film phase is precipitately formed proximal to the second surface so that the second surface is non-tacky. The film phase comprises at least one low surface energy, surface seeking moiety. A therapeutically effective amount of a pharmacologically active agent or prodrug form thereof is dispersed in the first, tacky phase.

In another aspect, the present invention relates to a method of in situ forming a covering element, as well as a covering element formed by the method, comprising coating a fluid composition onto a surface and causing the fluid component to dry. The fluid composition comprises: (i) an effective amount of a tacky component such that the formed covering element adheres to the surface; (ii) a film-forming, non-tacky component, wherein said film-forming, non-tacky component comprises at least one low surface energy, surface seeking moiety, wherein said film-forming, non-tacky component is incompatible with the tacky component, and wherein the film-forming, non-tacky component is present in an effective amount such that an outer surface of the in situ formed covering element is non-tacky when the covering element is touch dry; and (iii) a sufficient amount of at least one volatile solvent such that the fluid composition has a coatable viscosity allowing the fluid composition to be coated onto said surface. The resulting covering element comprises: (i) first and second opposed major surfaces; (ii) a first, tacky phase precipitately formed proximal to the first surface such that the first surface is sufficiently tacky to allow the covering element to be adhered to a surface of a host; and (iii) a second, non-tacky, film phase precipitately formed proximal to the second surface such that at least substantially all of the second surface is non-tacky, wherein the film phase comprises at least one low surface energy, surface seeking moiety.

The present invention further relates to a method of administering a pharmacologically active agent, or a prodrug thereof, to a host. Specifically, the method comprises coating a fluid composition onto a surface of the host, causing the coated fluid composition to dry such that a covering element is formed and maintaining contact between the covering element and the host surface in a manner such that the pharmacologically active agent is therapeutically administered to the host. The fluid composition comprises: (i) an effective amount of a tacky component such that the formed covering element adheres to the host surface; (ii) a film-forming, non-tacky component, wherein said film-forming, non-tacky component comprises at least one low surface energy, surface seeking moiety, wherein said film-forming, non-tacky component is incompatible with the tacky component, and wherein the film-forming, non-tacky component is present in an effective amount such that an outer surface of the in situ formed covering element is non-tacky when the covering element is touch dry; and (iii) a sufficient amount of at least one volatile solvent such that the fluid composition has a coatable viscosity allowing the fluid composition to be coated onto said host surface. The covering element comprises: (i) first and second opposed major surfaces; (ii) a first, tacky phase precipitately formed proximal to the first surface such that the first surface is sufficiently tacky to allow the covering element to be adhered to a surface of a host; and (iii) a second, non-tacky, film phase precipitately formed proximal to the second surface such that at least substantially all of the second surface is non-tacky, wherein the film phase comprises at least one low surface energy, surface seeking moiety; and (iv) a therapeutically effective amount of a pharmacologically active agent, or prodrug form thereof, dispersed in the first, tacky phase.

DETAILED DESCRIPTION OF THE PRESENTLY PREFERRED EMBODIMENTS

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

The present invention provides a unique approach of using coatable fluid compositions that may be applied onto a wide variety of surfaces and then dried to form, in situ, a protective and/or pharmacologically functional covering element. Advantageously, although applied as a fluid, these covering elements are formed in situ and have a protective, non-tacky, touch dry outer surface and a tacky bottom surface allowing the covering element to adhere to the desired surface. Although the fluid compositions, covering elements, and methods of the present invention can be used in a wide variety of different applications, the principles of the present invention are particularly advantageously used in connection with forming bandages or transtissue drug delivery systems for use on a host animal, preferably a mammal, more preferably a human.

Fluid compositions of the present invention may be in the form of an emulsion, foam, gel, solution, liquid, dispersion or the like. Fluid compositions of the present invention are preferably in the form of a solution. Depending upon the form of the fluid compositions, the fluid compositions may be coated onto the host animal at the desired location using any convenient coating technique, including by means of an aerosol, spraying, pumping, brushing, swabbing, combinations of these, or the like. Preferably, the fluid compositions are in the form of a solution comprising a propellant so that the fluid compositions can be sprayed onto the desired surface using aerosol spray techniques. For applications involving topical treatment of the skin or another exposed surface of a host, such as the oral tissue, the fluid composition may be coated directly over the treatment site. For topical applications in which the fluid composition will be used to form a protective bandage over a wound, the wound area optionally may first be covered with a pad or other covering. Such pad then may be securely held in place over the wound by forming a covering element of the present invention over the pad and adjacent areas of the host. For transtissue drug delivery applications, a fluid composition incorporating the desired pharmacologically active agent (or prodrug form thereof) and optionally other beneficial excipients (e.g., a penetration enhancer, emulsifier, antioxidant, surfactant, or the like) may be coated onto the desired delivery site and then dried to form a covering element. For example, the covering element may be formed on intact skin for transdermal drug delivery, or on a mucosal membrane for drug delivery through such membrane. Non-invasive drug delivery then occurs as contact between the covering element and the tissue is maintained.

A coatable composition for in situ forming a covering element according to the principles of the present invention generally includes an effective amount of a tacky component such that the formed covering element adheres to the desired surface on which the covering element is to be used. If too little of the tacky component is incorporated into the fluid composition, the covering element may show poor adhesion to the desired substrate surface. Additionally, because it is believed that the pharmacologically active agent, when used, is primarily incorporated into the tacky phase of the covering element, using too little of the tacky component may also unduly limit the amount of the pharmacologically active agent that can be incorporated into the covering element. On the other hand, if too much of the tacky component is used, then the top, exposed surface of the resultant covering element may be undesirably tacky. Additionally, if too much of the tacky component is used, the fluid composition may be too viscous to be coated onto the desired surface using the desired coating technique. Balancing these concerns, fluid compositions of the present invention typically incorporate from about 1 to about 50, preferably about 5 to about 20, more preferably from about 5 to about 10 weight percent of the tacky component based upon the total weight of the fluid composition.

A wide variety of tacky materials, or precursor materials that form a tacky material in situ, may be used as the tacky component. Desirably, the tacky component is substantially inert with respect to the other components of the fluid composition, particularly the pharmacologically active agent, or prodrug form thereof, if any. For therapeutic applications, the tacky component should adhere well to the desired treatment site of the host animal on which the corresponding covering element will be formed. Preferably, the tacky component is waterproof so that the covering element remains adhered to the host for the desired treatment period, but should be releasable so that the covering element can be removed when the treatment involving that covering element is completed. The tacky component should also be compatible with the host so that undue irritation at the treatment site is avoided. The tacky material preferably is sufficiently flexible to allow the covering element to conform to and follow the contours of the treatment site without cracking and without causing undue restriction of host movement.

A particularly beneficial class of tacky materials meeting these criteria is the class of (meth) acrylate polymers, preferably acrylate embodiments thereof, suitable for use as pressure sensitive adhesives (PSA's). Representative embodiments of such (meth)acrylate PSA's are described in U.S. Pat. Nos. 4,751,087; 4,737,577; and Re 24,906; and in Assignee's copending U.S. patent application Ser. No. 08/968519 filed Nov. 12, 1997 in the names of James E. Garbe et al.; all of which are incorporated herein by reference in their respective entireties.

A (meth)acrylate PSA suitable in the practice of the present invention preferably has a weight average molecular weight that is high enough so that the polymer has good handling, performance, and mechanical properties. However, if the weight average molecular weight of the (meth)acrylate PSA is too high, fluid compositions incorporating such adhesive may have a viscosity that is too high for the desired coating technique. Accordingly, a preferred (meth)acrylate PSA generally has a weight average molecular weight in a range such that the adhesive has an inherent viscosity in the range from about 0.2 dl/g to about 2 dl/g, more preferably from about 0.4 dl/g to about 1.4 dl/g. Inherent viscosity may be determined by conventional means using a Canon-Fenske #50 viscometer in a water bath controlled at 27° C. to measure the flow of 10 ml of polymer solution.

A particularly preferred (meth)acrylate PSA is a copolymer derived from monomers comprising, based upon the total weight of the copolymer, about 40 to about 100, preferably about 50 to about 75, weight percent of an alkyl (meth)acrylate (A monomer) and 0 to about 60, preferably about 25 to about 50, weight percent of a free radically copolymerizable monomer (B monomer). Optionally, other monomers may also be incorporated into the copolymers. Such other monomers, for example, may further include up to about 30 weight percent, preferably up to about 15 weight percent, of a copolymerizable macromonomer as described in Assignee's copending U.S. patent application having U.S. Ser. No. 08/523762, identified above.

The A monomer preferably is selected from one or more alkyl (meth)acrylates containing 1 to about 10 carbon atoms in the alkyl group. Representative examples of the alkyl (meth)acrylate monomer include methyl (meth)acrylate, n-butyl (meth)acrylate, n-pentyl (meth)acrylate, n-hexyl (meth)acrylate, isoheptyl (meth)acrylate, cyclohexyl (meth) acrylate, n-nonyl (meth)acrylate, n-decyl (meth)acrylate, isohexyl (meth)acrylate, 2-ethyloctyl (meth)acrylate, isooctyl (meth)acrylate, isobornyl (meth)acrylate, and 2-ethylhexyl (meth)acrylate. Combinations of these can be used if desired. Preferably, the alkyl (meth)acrylate is selected from isooctyl (meth)acrylate, butyl methacrylate, 2-ethylhexyl (meth)acrylate, cyclohexyl methacrylate, isobornyl methacrylate, and methyl methacrylate.

The copolymerizable B monomer is generally one or more (meth)acrylate monomers having at least one functional group selected from the grouping consisting of carboxylic acid, carboxylic acid ester, hydroxyl, anydride, epoxy, thiol, isocyanate, sulfonamide, urea, carbamate, carboxamide, amine, ammonium, oxy, oxo, nitro, nitrogen, sulfur, phosphate, phosponate, cyano, combinations of these, and the like. Representative examples of specific materials that can be used singly or in combination as the B monomer include (meth)acrylic acid, maleic acid, vinyl acetate, a hydroxyalkyl (meth)acrylate containing about 2 to about 4 carbon atoms in the hydroxyalkyl group, (meth) acrylamide, an alkyl substituted (meth)acrylamide having 1 to about 8 carbon atoms in the alkyl group, diacetone (meth)acrylamide, a dialkyl (meth)acrylamide independently having 1 or 2 carbon atoms in each alkyl group, N-vinyl-N-methyl acetamide, N-vinyl valerolactam, N-vinyl caprolactam, N-vinyl-2-pyrrolidone, glycidyl (meth)acrylate, alkoxy (meth)acrylate containing 1 to 4 carbon atoms in the alkoxy group, 2-ethoxyethyl (meth) acrylate, 2,2-ethoxyethoxyethyl (meth)acrylate, furfuryl (meth)acrylate, tetrahydrofurfuryl (meth)acrylate, propylene glycol mono(meth)acrylate, polyethylene glycol (meth) acrylate, polyethylene glycol methyl ether (meth)acrylate, polyethylene oxide methyl ether (meth)acrylate, di(lower) alkylaminopropyl (meth)acrylamide (wherein lower means the alkyl moiety has 1 to 4 carbon atoms), (meth) acrylonitrile, combinations of these, and the like. Preferably, the copolymerizable B monomer is selected from hydroxyethyl acrylate, hydroxyethyl methacrylate, acrylamide, glyceryl acrylate, N,N-dimethyl acrylamide, 2-ethoxyethyl acrylate, 2,2-ethoxyethoxyethyl acrylate, tetrahydrofurfuryl acrylate, vinyl acetate, and acrylic acid. Any of the aforementioned alkyl groups may be linear, branched or cyclic.

One particularly preferred (meth)acrylate PSA is a copolymer formed by copolymerizing about 60 to about 80, preferably about 75 weight percent of isooctyl (meth) acrylate (preferably the acrylate form); about 1 to about 10, preferably about 5 weight percent of (meth)acrylamide (preferably the acrylate form); and about 5 to about 30, preferably about 20 weight percent of vinyl acetate. This (meth)acrylate PSA demonstrates excellent adhesion to the skin of a human or other animal host, is flexible and waterproof, is soluble in therapeutically compatible solvents such as isopropyl alcohol, is very compatible with many kinds of pharmacologically active agents, and demonstrates a desirable level of incompatibility/immiscibility with the non-tacky, film-forming component of the fluid composition to be described below. Other preferred (meth)acrylate PSA polymers are formed from monomers according to formulations summarized in the following table:

| PSA Sample | Parts by weight: | | | | | | |
|---|---|---|---|---|---|---|---|
| | IOA | ACM | VOAc | DMACM | AA | HEA | NVP |
| 1 | 93 | 7 | — | — | — | — | — |
| 2 | 70 | — | — | 30 | — | — | — |
| 3 | 63 | — | 37 | — | — | — | — |
| 4 | 80 | — | — | — | 20 | — | — |
| 5 | 60 | — | — | — | — | 40 | — |
| 6 | 91 | — | — | — | — | — | 9 |
| 7 | 89 | — | — | — | — | 2 | 9 | wherein IOA is isooctyl acrylate, ACM is acrylamide, VOAc is vinyl acetate, DMACM is N,N-dimethylacrylamide, AA is acrylic acid, HEA is 2-hydroxyethyl acrylate, and NVP is N-vinylpyrrolidone.

The particularly preferred (meth)acrylate PSA may be prepared by free-radical polymerization methods known in the art, including but not limited to bulk, solution, emulsion and suspension polymerization methods. For example, according to the solution polymerization method, copolymers suitable for use in the present invention are prepared by dissolving the desired monomers in an appropriate solvent, adding a chain-transfer agent, a free-radical polymerization initiator, and other additives known in the art, sealing the solution in an inert atmosphere such as nitrogen or argon, and then agitating the mixture at a temperature sufficient to activate the initiator.

Solvents useful in such polymerizations can vary according to solubility of the monomers and additives. Typical solvents include ketones such as acetone, methyl ethyl ketone, 3-pentanone, methyl isobutyl ketone, diisobutyl ketone, and cyclohexanone; alcohols such as methanol, ethanol, propanol, n-butanol, isopropanol, isobutanol, cyclohexanol and methyl cyclohexanol; esters such as ethyl acetate, butyl acetate, isobutyl acetate, isopropyl acetate, and the like; aromatic hydrocarbons such as benzene, toluene, xylenes, cresol, and the like; ethers such as diisopropyl ether, diisobutyl ether, tetrahydrofuran, tetrahydropyran, and dioxane; and aprotic solvents such as dimethylformamide, dimethylsulfoxide and the like, and mixtures thereof.

Chain transfer agents suitable for solution polymerization include but are not limited to alcohols, mercaptans, certain halogenated small molecules, and mixtures thereof. Preferably, the chain transfer agent is chosen from the group consisting of carbon tetrabromide, isooctylthioglycolate, mercaptosuccinic acid, mercaptopropane diol, dodecyl mercaptan, ethanol and carbon tetrachloride. Most preferably, the chain transfer agent is mercaptopropane diol.

Free-radical polymerization initiators suitable for solution polymerization include those that are soluble in the reaction solvent and that are thermally activated, including but not limited to azo compounds, peroxides, and mixtures thereof. Useful peroxide initiators include those chosen from the group consisting of benzoyl peroxide, lauroyl peroxide, di-t-butyl peroxide and the like, and mixtures thereof. Useful azo compound initiators include those chosen from the group consisting of 2,2'-azobis(2-methylbutyronitrile); 2,2'azobis(isobutyronitrile); and 2,2'-azobis(2,4-dimethylpentanenitrile); each of which is commercially available as VAZO 67, VAZO 64, and VAZO 52, respectively, from E.I. DuPont de Nemours & Co., Wilmington, Del.

The (meth)acrylate PSA polymers of the present invention may also be prepared by emulsion polymerization methods. According to the emulsion polymerization method, polymers suitable for use in the present invention are prepared by forming an emulsion comprising the desired monomers, a chain-transfer agent and a water-soluble redox-type initiator system in an inert atmosphere such as nitrogen or argon, and then heating the emulsion carefully until a reaction exotherm occurs. The reaction mixture is stirred and cooled and the resulting polymer is collected. Optionally, an ionic or nonionic surfactant may be added to the reaction mixture. Oxidation—reduction ("Redox") free-radical initiators may also optionally be added. Redox initiators suitable for use in the fluid compositions of the present invention include, but are not limited to, those chosen from the group consisting of tertiary amines with organic peroxides (exemplified by the N,N-diethylaniline—benzoyl peroxide pair); organic halides with transition metal complexes (exemplified by the carbon tetrachloride—molybdenum hexacarbonyl pair); inorganic oxidation—reduction systems (exemplified by the potassium persulfate—sodium metabisulfite pair); and organic—inorganic systems (exemplified by the 2-mercaptoethanol—$Fe^{+3}$ pair). Inorganic redox initiators are preferred for the copolymers of the invention because of their ease of handling and useful reaction temperature range.

The fluid composition of the present invention also includes a film-forming, non-tacky component that is incompatible with the tacky component. As used herein, the terms "incompatible" or "immiscible" mean that a solution comprising the tacky and non-tacky components undergoes phase separation during drying such that the resultant dried coating, i.e., covering element, comprises at least a first tacky phase and a second non-tacky phase. The tacky characteristics of the first phase are imparted by the presence of the tacky component in the first phase (even though minor amounts of the non-tacky component may also be present if the two different components are not 100% immiscible with each other), and the non-tacky characteristics of the second phase are imparted by the presence of the non-tacky component in the second phase (even though minor amounts of the tacky component may also be present if the two components are not 100% immiscible with each other). For purposes of the present invention, a dried coating or covering element preferably refers to a coating comprising less than about 5 weight percent, preferably less than about 2 weight percent, and more preferably less than about 0.5 weight percent, of solvent based upon the total weight of the coating.

Representative examples of film forming, non-tacky polymers that may be incorporated singly or in combination into the non-tacky component include one or more, cellulosic polymers such as ethyl cellulose and nitrocellulose, siloxane containing polymers such as silicone polyureas and silicone polyurethanes, polyvinylacetate, polymethyl(meth)acrylate, fluorinated polymers such fluorinated (meth)acrylates and polyvinylidene fluoride, fluorosilicone polymers, styrene-butadiene rubbers, polyurethanes, vinyl copolymers, polyolefins, polyamides, polyimides, polyamideimides, polyesters combinations of these, and the like. Choosing a suitable non-tacky component will depend to a large extent upon the nature of the tacky component, because the two components are desirably at least partially, preferably at least substantially, more preferably completely, immiscible with each other. Desirably, one or more of such film forming, flexible polymers are selected for incorporation into the non-tacky component so that the non-tacky phase of the resultant covering element is sufficiently flexible and elastomeric so as to be conformable to the surface of a host animal without cracking or delaminating during host movement. It is further desirable that the non-tacky phase tends to precipitatively form during phase separation proximal to the top, exposed surface of the covering element, whereas the tacky phase tends to form proximal to the bottom of the covering element. As a result of this desired characteristic, a fluid composition of the present invention unexpectedly and advantageously dries to form a covering element with a non-tacky, protective film as an outer surface while having a tacky bottom surface that helps to adhere the covering element to the desired surface.

Precipitative formation of the non-tacky phase proximal to the top of the covering element can be achieved in a variety of ways. As one exemplary approach, the polymer(s) incorporated into the non-tacky component may be selected so as to have a density that is less than that of the one or more polymers incorporated into the tacky component. In this way, density effects cause the non-tacky polymer(s) to rise to the top of the coated fluid composition, where those polymer(s) then precipitate as the coating dries.

As another more preferred approach to be used singly or in combination with density effects, non-tacky polymers can be selected which include one or more different kinds of moieties that tend to seek the surface of the coating (due to low surface energy effects) as a blend of the tacky and non-tacky components phase separate during drying. For example, in embodiments of the present invention in which the tacky component comprises a (meth)acrylate PSA, preferred non-tacky components include one or more polymers comprising at least one siloxane moiety and/or at least one fluorine containing moiety. Preferred fluorine containing moieties are perfluorinated. Siloxane and fluorine-containing moieties both tend to migrate to the surface of a coating in order to achieve as low a surface energy as possible. As the surface seeking moiety migrates to the top of the coating, the non-tacky polymer that incorporates the moiety tends to migrate with it. As a result, when the non-tacky and tacky components phase separate and precipitate as the coated composition dries, the phase that is rich with the non-tacky, film-forming component tends to precipitatively form proximal to the top of the covering element. On the other hand, the phase that is relatively rich with the tacky component tends to precipitatively form more proximal to the interface between the coating and the substrate surface.

When the tacky component comprises an acrylate PSA, the non-tacky component most preferably comprises a siloxane containing polymer such as a silicone polyurea or silicone polyurethane block polymer. Silicone polyurea/urethane block polymers, in particular, have a number of desirable properties. For example, such polymers are soluble in therapeutically compatible solvents such as isopropanol. These polymers are also immiscible with (meth)acrylate PSA's, facilitating the desired phase separation between the two materials. The polymers are also relatively impermeable to many pharmacologically active agents, helping to keep such agents from diffusing out the top of a corresponding cover element. The siloxane moiety of these polymers is incompatible with (meth)acrylate PSA's and strongly seeks the surface of a coating to achieve a low surface energy. The polymers also have hard and soft domains for a good balance of physical and mechanical properties. For example, the urea/urethane segments physically crosslink to give a covering element incorporating these polymers a good combination of flexibility, strength and durability. Additionally, films of these polymers are waterproof, yet transmittant to water vapor.

As used herein, a preferred silicone polyurea/urethane block polymer refers to a polymer comprising one or more siloxane units (corresponding to surface seeking, soft segments), preferably in the form of polysiloxane units, and one or more units comprising a urea, urethane, and/or urethane-urea linkage (corresponding to hard segments). A representative poloysiloxane unit is

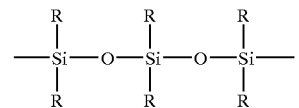

wherein each R independently is typically a linear, branched or cyclic alkyl or aryl radical or combinations thereof. A representative hard segment structure is

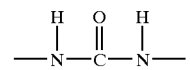

The urea and/or siloxane units may be incorporated into the main backbone of the polymer or may be pendant from the main backbone as desired. One skilled in the art will recognize that the terms "siloxane" and "urea" encompass structures which may differ slightly than those given by way of example above. For example, siloxane moieties are generally described in Carraher, C. E., Jr., *Seymour/Carraher's Polymer Chemistry: An Introduction*, 4$^{th}$ ed., Marcel Dekker, Inc., 1996, at pages 337,338, 355, and 454–456, incorporated herein by reference. Generally, the polysiloxane content of the block polymer will be in the range of about 1 to about about 95 weight percent, preferably about 5 to about 50 weight percent, and most preferably about 20 to about 30 weight percent, based upon the total weight of the block polymer.

Particularly preferred embodiments of silicone-urea block copolymers are derived from monomers comprising:

(1) a polyfunctional nucleophile comprising at least two moieties copolymerizable with NCO moieties and a siloxane moiety. Such a nucleophile preferably is a diamine functional or dihydroxy functional siloxane having a number average molecular weight of at least 500, and preferably a structure represented by the formula

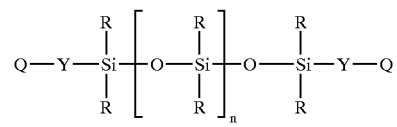

wherein Q is —OH or

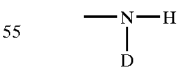

and R, Y, D and n are as defined below;

(2) at least one diisocyanate preferably having a structure represented by the formula

wherein Z is as defined below; and (3) optionally, up to about 95 weight percent, preferably about 50 to about 70 weight percent of a chain extender component having two or more moieties (e.g., amine moieties, hydroxyl moieties, or a combination thereof) that are reactive with NCO, and having a number average molecular weight preferably in the range from about 50 to about 500, preferably about 2000, and preferably selected from the group consisting of a diamine chain extender, a diol chain extender, and mixtures thereof and preferably having a structure represented by the formula

H-A-B-A-H wherein A and B are as defined below. The molar ratio of the total moles of chain extender and siloxane-containing polyfunctional nucleophile to the diisocyanate is preferably in the range of about about 0:9:1 to about 1:0.9, and most preferably is about 1:1.

A specific example of a preferred silicone-urea block polymer polymerized from such monomers has the structure

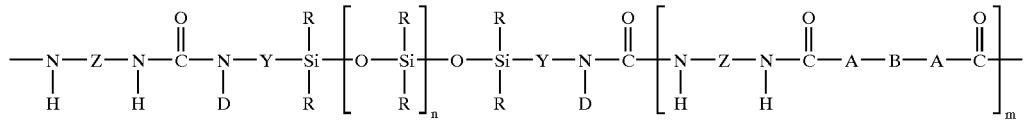

wherein:

Z is a divalent radical selected from the group consisting of phenylene, alkylene, aralkylene and cycloalkylene; Z is preferably selected from the group consisting of hexamethylene; methylene bis-(phenylene); isophorone; tetramethylene; cyclohexylene; and methylene dicyclohexylene; and most preferably is isophorone;

Y is an alkylene radical of 1 to 10 carbon atoms; preferably Y is propylene;

R is at least about 50% methyl with the balance of the 100% of all R radicals being selected from the group consisting of methyl, a monovalent alkyl radical having from 2 to 12 carbon atoms, a vinyl radical, a phenyl radical, and a substituted phenyl radical; preferably R is methyl or a monovalent alkyl radical having from 2 to 12 carbon atoms; and most preferably R is methyl;

D is selected from the group consisting of hydrogen, and an alkyl radical of 1 to 10 carbon atoms; preferably D is hydrogen;

B is selected from the group consisting of alkylene, aralkylene, cycloalkylene, azaalkylene, cycloazaalkylene, phenylene, polyalkylene oxides, polyethylene adipate, polycaprolactone, polybutadiene, a radical completing a ring structure including A to form a heterocycle and mixtures thereof; preferably B is a polyalkylene oxide and/or alkylene;

A is selected from the group consisting of the structures

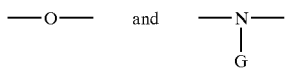

or combinations thereof, wherein G is selected from the group consisting of hydrogen, an alkyl radical of 1 to 10 carbon atoms, phenyl, a radical which completes a ring structure including B to form a heterocycle and mixtures thereof, preferably G is hydrogen, a radical which forms a ring structure including B to form a heterocycle or mixtures thereof;

n is an integer which is 4 or larger, preferably 65 or larger; and m is an integer which is from zero to 25.

As used herein, the term "radical" includes organic radicals which may be straight, branched, or cyclic and which may be substituted as well as unsubstituted, e.g., halo- or CN-substituted radicals.

In a preferred embodiment of the present invention, the silicone-urea block polymer is prepared by condensation polymerization and will comprise segments derived from monomers comprising polydimethysiloxane diamine (PDMS); 1,3-diaminopentane (DAMP), isophorone diisocyanate (IPDI), and polypropylene oxide (PPO) with terminal diamine groups. The preferred formulations (in weight percent based upon the total weight of the silicone-urea block polymer) of PDMS diamine, DAMP, IPDI, and PPO, are as follows:

| PDMS diamine | DAMP/IPDI* | PPO |
|---|---|---|
| 20 | 25 | 55 |
| 20 | 30 | 50 |
| 20 | 35 | 45 |

*The weight ratio of IPDI to DAMP is selected so that the molar ratio of NCO groups to amine groups of the PDMS diamine, DAMP and PPO is 0:9:1 to 1:0.9, preferably 1:1.

Silicone-urea block polymers are known in the art and may be prepared by any suitable method such as condensation polymerization. See, e.g., U.S. Pat. Nos. 5,214,119; 5,290,615; 5,461,134; 5,512,650; 5,670,598; and 5,750,630; and international patent publication No. WO 96-34029 (Mazurek et al.), all of which are incorporated herein by reference in their respective entireties. The preferred silicone-urea block polymers of the present invention may be prepared by the condensation polymerization of the components disclosed below. Generally, the polymerization reaction is carried out in an alcohol based solvent, such as isopropanol, at room temperature, preferably under an inert atmosphere such as nitrogen or argon.

The film-forming, non-tacky component preferably is present in an effective amount such that an outer surface of the in situ formed covering element is non-tacky when the covering element is dried. The optimum amount of the non-tacky component required to achieve this objective will depend upon a variety of factors including the amount and type of the tacky component, the amount and type of penetration enhancer, if any, and the amount and type of solvent, if any, and the like. As general guidelines, the weight ratio of the tacky component to the non-tacky component is generally in the range from about 1:20 to about 20:1, preferably about 1:10 to about 10:1 more preferably about 3:5 to about 5:3.

The fluid composition may further optionally include a sufficient amount of at least one volatile solvent such that the fluid composition has a viscosity effective to allow the fluid composition to be coated onto the desired surface using the desired coating technique. The amount of solvent required to provide a suitable, coatable viscosity will depend to a large extent upon the type of method that is used to apply the fluid composition onto a host surface. For instance, a fluid composition that is to be applied as an emulsion or gel would tend to have a higher viscosity than a fluid composition that is to be sprayed as an aerosol. One skilled in the art can determine an appropriate amount of solvent needed to provide a desired coating viscosity in accordance with conventional practices. As suggested guidelines, preferred fluid compositions generally may comprise about 5 to about 40 weight percent of solvent, preferably include about 5 to about 20 weight percent of solvent, based upon the total weight of the composition.

Preferred volatile solvents are desirably therapeutically safe and skin tolerant. Such solvents also desirably should be nonflammable, yet should have a sufficiently high vapor pressure under ambient conditions such that a coating of the fluid composition is touch dry within 10 minutes, preferably 3 minutes, more preferably 1 minute, after being coated onto a surface. Such solvents also desirably solvate at least one, and preferably all, of the components of the fluid composition so that the composition can be coated onto the desired surface as a homogeneous slurry, dispersion, or solution, as the case may be.

Selecting a suitable volatile solvent for a particular application will depend upon a variety of factors including the nature of the other ingredients of the fluid composition, the manner in which the fluid composition is to be coated onto a surface, the intended use of the resultant covering element, and the like. One skilled in the art would be able to select a suitable volatile solvent in accordance with conventional practices and with due consideration to these factors from among solvents such as 2-methyl butane, pentane, hexane, dimethoxcymethane, cyclopentane, acetone, methyl acetate, ethyl acetate, 2,3-dimethyl butane, 2,2-dimethyl butane, 2-methyl pentane, 3-methyl pentane, ethanol, isopropanol, hexamethyldisiloxane, water, combinations of these, and the like. For applications in which the fluid composition comprises a (meth)acrylate PSA and a silicone-urea block copolymer, a preferred solvent is selected from ethanol, acetone, isopropanol, or combinations thereof. Of these, isopropanol is most preferred. A co-solvent comprising about 1 to about 100, preferably about 10, parts by weight ethanol per about 1 to about 100, preferably about 90, parts by weight of hexamethyldisiloxane is also preferred.

In addition to the tacky component, the non-tacky component, and optionally, the volatile solvent, the fluid composition of the present invention may further comprise other ingredients that may enhance the function and performance of the fluid composition. For example, in applications involving topical and/or transtissue drug delivery, the fluid composition may further comprise a therapeutically effective amount of a pharmacologically active agent or prodrug form thereof. The amount that constitutes a therapeutically effective amount varies according to a number of factors including the particular pharmacological agent(s) being used, the condition being treated, the characteristics of the host, any drugs being coadministered, desired duration of treatment, surface of the host at which the covering element is to be placed, other components of the fluid composition, and the like. An appropriate therapeutic dosage can be determined by one skilled in the art with due consideration given to such factors. As general guidelines, however, a typical therapeutic amount may in the range of about 0.01 to about 30 percent by weight based upon the total weight of the nonsolvent components of the fluid composition. Preferably, the pharmacologically active agent is substantially fully dissolved in the fluid composition and/or is in liquid form when combined with the other ingredients such that the fluid composition is substantially free of any solid, undissolved pharmacologically active agent.

As used herein, "pharmacologically active agent" generally refers to an agent having a direct or indirect pharmacological effect upon a host. A "prodrug form" of a pharmacologically active agent means a structurally related compound or derivative of an active compound which, when topically applied or delivered transtissually (e.g. transdermally delivered through intact skin or absorbed through a mucosal membrane) to a host is converted into the desired pharmacologically active agent. The prodrug form itself may have little or none of the pharmacologically desired activity.

Representative examples of pharmacologically active agents that may be suitable for use in the fluid compositions of the present invention include (grouped by therapeutic class):

Antidiarrhoeals such as diphenoxylate, loperamide and hyoscyamine;

Antihypertensives such as hydralazine, minoxidil, captopril, enalapril, clonidine, prazosin, debrisoquine, diazoxide, guanethidine, methyldopa, reserpine, trimethaphan;

Calcium channel blockers such as diltiazem, felodipine, amlodipine, nitrendipine, nifedipine and verapamil;

Antiarrhyrthmics such as amiodarone, flecainide, disopyramide, procainamide, mexiletene and quinidine;

Antiangina agents such as glyceryl trinitrate, erythrityl tetranitrate, pentaerythritol tetranitrate, mannitol hexanitrate, perhexilene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glyceryl trinitrate, pentaerythritol tetranitrate and xanthinol;

Antimigraine preparations such as ergotamine, dihydroergotamine, methysergide, pizotifen and sumatriptan;

Anticoagulants and thrombolytic agents such as warfarin, dicoumarol, low molecular weight heparins such as enoxaparin, streptokinase and its active derivatives;

Hemostatic agents such as aprotinin, tranexamic acid and protamine;

Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenoperidine, codeine dihydrocodeine; acetylsalicylic acid (aspirin), paracetamol, and phenazone;

Hypnotics and sedatives such as the barbiturates amylobarbitone, butobarbitone and pentobarbitone and other hypnotics and sedatives such as chloral hydrate, chlormethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl) indole;

Anti-alzheimer's agents such as tacrine;

Anti-Parkinson's agents such as amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetralin (N-0923);

Anticonvulsants such as phenytoin, valproic acid, primidone, phenobarbitone, methylphenobarbitone and carbamazepine, ethosuximide, methsuximide, phensuximide, sulthiame and clonazepam;

Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and brompride;

Non-steroidal anti-inflammatory agents including their racemic mixtures or individual enantiomers where applicable, preferably which can be formulated in combination with dermal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaemia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;

Antioestrogens such as tamoxifen and epitiostanol and the aromatase inhibitors, exemestane and 4-hydroxyandrostenedione and its derivatives;

Androgens and anabolic agents such as testosterone, methyltestosterone, clostebol acetate, drostanolone, furazabol, nandrolone oxandrolone, stanozolol, trenbolone acetate, dihydro-testosterone, 17-α-methyl-19-nortestosterone and fluoxymesterone;

5-alpha reductase inhibitors such as finasteride, turosteride, LY-191704 and MK-306;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;

Further examples of steroidal antiinflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

Pituitary hormones and their active derivatives or analogs such as corticotrophin, thyrotropin, follicle stimulating hormone (FSH), luteinising hormone (LH) and gonadotrophin releasing hormone (GnRH);

Hypoglycemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil;

Other miscellaneous hormone agents such as octreotide;

Pituitary inhibitors such as bromocriptine;

Ovulation inducers such as clomiphene;

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene;

Antidiuretics such as desmopressin, lypressin and vasopressin including their active derivatives or analogs;

Obstetric drugs including agents acting on the uterus such as ergometrine, oxytocin and gemeprost;

Prostaglandins such as alprostadil (PGE1), prostacyclin (PGI2), dinoprost (prostaglandin F2-alpha) and misoprostol;

Antimicrobials including the cephalosporins such as cephalexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;

Tetracyclines such as minocycline, chlortetracycline, tetracycline, demeclocycline, doxycycline, methacycline and oxytetracycline and other tetracycline-type antibiotics;

Aminoglycosides such as amikacin, gentamicin, kanamycin, neomycin, netilmicin and tobramycin;

Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;

Quinolones such as nalidixic acid, cinoxacin, ciprofloxacin, enoxacin and norfloxacin;

Sulphonamides such as phthalysulphthiazole, sulfadoxine, sulphadiazine, sulphamethizole and sulphamethoxazole;

Sulphones such as dapsone;

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoylperoxide;

Antituberculosis drugs such as ethambutol, isoniazid, pyrazinamide, rifampicin and clofazimine;

Antimalarials such as primaquine, pyrimethamine, chloroquine, hydroxychloroquine, quinine, mefloquine and halofantrine;

Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Anthelmintics such as mebendazole, thiabendazole, niclosamide, praziquantel, pyrantel embonate and diethylcarbamazine;

Cytotoxic agents such as plicamycin, cyclophosphamide, dacarbazine, fluorouracil and its prodrugs (described, for example, in International Journal of Pharmaceutics 111, 223–233 (1994)), methotrexate, procarbazine, 6-mercaptopurine and mucophenolic acid;

Anorectic and weight reducing agents including dexfenfluramine, fenfluramine, diethylpropion, mazindol and phentermine;

Agents used in hypercalcaemia such as calcitriol, dihydrotachysterol and their active derivatives or analogs;

Antitussives such as ethylmorphine, dextromethorphan and pholcodine;

Expectorants such as carbolcysteine, bromhexine, emetine, quanifesin, ipecacuanha and saponins;

Decongestants such as phenylephrine, phenylpropanolamine and pseudoephedrine;

Bronchospasm relaxants such as ephedrine, fenoterol, orciprenaline, rimiterol, salbutamol, sodium cromoglycate, cromoglycic acid and its prodrugs (described, for example, in International Journal of Pharmaceutics 7, 63–75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

Local anaesthetics such as bupivacaine, amethocaine, lignocaine, lidocaine, cinchocaine, dibucaine, mepivacaine, prilocaine; etidocaine; and procaine;

Stratum corneum lipids, such as ceramides, cholesterol and free fatty acids, for improved skin barrier repair [Man, et al. J. Invest. Dermatol., 106(5), 1096, (1996)];

Neuromuscular blocking agents such as suxamethonium, alcuronium, pancuronium, atracurium, gallamine, tubocurarine and vecuronium;

Smoking cessation agents such as nicotine, bupropion and ibogaine;

Insecticides and other pesticides which are suitable for local or systemic application;

Dermatological agents, such as vitamins A, C, $B_1$, $B_2$, $B_6$, $B_{12a}$ and E, vitamin E acetate and vitamin E sorbate;

Allergens for desensitisation such as house, dust or mite allergens;

Nutritional agents, such as vitamins, essential amino acids and essential fats;

Keratolytics such as the alpha-hydroxy acids, glycollic acid and salicylic acid;

Anti-acne agents such as isotretinoin, tretinoin and benzoyl peroxide;

Anti-psoriasis agents such as etretinate, cyclosporin and calcipotriol;

Anti-itch agents such as capsaicin and its derivatives such as nonivamide [Tsai, et al. Drug. Dev. Ind. Pharm., 20(4), 719, 1994];

Anticholinergic agents, which are effective for the inhibition of axillary sweating and for the control of prickly heat;

Antiperspirant agents such as methatropine nitrate, propantheline bromide, scopolamine, methscopolamine bromide, and quaternary acyloxymethyl ammonium salts (described, for example, by Bodor et al, J. Med. chem. 23, 474 (1980) and also in United Kingdom Specification No. 2010270, published 27 Jun. 1979); and Other pharmacologically active peptides and proteins, small to medium-sized peptides, e.g., vasopressin and human growth hormone.

Embodiments of the fluid composition comprising a pharmacologically active agent and intended to be used for transtissue drug delivery preferably further include a penetration enhancer. A penetration enhancer is an agent that improves the transtissue penetration rate of a pharmacologically active agent through a tissue such as skin, a mucosal membrane, or other tissue, whether such transtissue drug delivery is intended for local or systemic delivery. Generally, the fluid composition comprises a sufficient amount of the penetration enhancer to cause drug delivery to occur at the desired rate. The amount of a penetration enhancer required to achieve such an objective can be determined by one skilled in the art in accordance with conventional practices. In determining a suitable amount of penetration enhancer to be used, the skilled worker would give due consideration to factors such as the nature of the other ingredients of the fluid composition, the nature of the penetration enhancer, the nature of the host surface on which the fluid composition will be coated to form a covering element, and the like. As general guidelines, preferred fluid compositions of the present invention include about 1 to about 50, preferably about 5 to about 40, more preferably about 10 to about 30 parts by weight of the penetration enhancer per 100 parts by weight of the tacky component of the fluid composition.

Representative examples of penetration enhancers include sunscreen esters of the type described in PCT Publication WO 97/29735, laurocapram and its derivatives such as 1-alkylazacycoheptan-2-ones as described in U.S. Pat. No. 5,196,410; oleic acid and its ester derivates such as methyl oleate, ethyl oleate, propyl oleate, isopropyl oleate, butyl oleate, vinyl oleate, and glyceryl monooleate; sorbitan esters such as sorbitan monolaurate and sorbitol monooleate; other fatty acid esters such as glyceryl monolaurate, isopropyl laurate, isopropyl myristate, isopropyl palmitate, diisopropyl adipate, propylene glycol monolaurate, and propylene glycol monooleate; long chain alkyl esters of 2-pyrrolidone, such as 1-lauryl, 1-hexyl, and 1-(2-ethylhexyl)ester of 2-pyrrolidone; a penetration enhancer of the type described in U.S. Pat. No. 5,082,866 such as dodecyl (N,N-dimethylamino) acetate and dodecyl (N,N dimethylamino) propionate; a penetration enhancer as described in U.S. Pat. No. 4,861,764 such as 2-n-nonyl-1-3-dioxolane; combinations of these, and the like. A particularly preferred penetration enhancer includes 10 to 70 parts by weight of isopropyl myristate, about 1 to about 25 parts by weight of glyceryl monolaurate, and about 5 to about 70 parts by weight of ethyl oleate per 100 parts by weight of the penetration enhancer.

Fluid compositions intended to be applied to a surface by spraying as an aerosol may also optionally incorporate a propellant. A preferred propellant is generally a halogenated hydrocarbon, fluorinated hydrocarbon, ether, or inert gas that is miscible with at least one of, preferably all of, the volatile solvent, the tacky component, and/or the non-tacky component. Specific examples of propellants generally include carbon dioxide, compressed air, 2-hydroperfluoropropane, tetrafluoroethane, perfluoropropane, octafluorocyclobutane, difuoroethane, dimethyl ether, butane, nitrogen, combinations of these, and the like. In embodiments of the invention in which the fluid composition comprises a (meth)acrylate PSA and a silicone polyurea or silicone polyurethane block polymer, the propellant is preferably dimethyl ether. Dimethyl ether easily solvates both types of materials, has moderate vapor pressure, and has low toxicity. Fluorinated hydrocarbons, butane, and nitrogen do not, by themselves, solvate acrylate PSA materials, and thus are less preferred in such embodiments unless used in combination with one or more other solvating propellants. As general guidelines, a fluid composition may include about 40 to about 85, preferably about 50 to about 75 parts by weight of propellant per 100 parts by weight of the fluid composition.

Fluid compositions of the present invention may also further comprise one or more additional adjuvants in accordance with conventional practices. Examples of such adjuvants include a pharmaceutical compounding agent, a surfactant, an emulsifier, an antioxidant, a preservative, a stabilizer, a diluent, or combination of these.

To make a fluid composition of the present invention, the components are combined and mixed until a homogeneous solution, slurry, dispersion, gel, or the like, as the case may be, is obtained. For example, to make a particularly preferred fluid composition that can be sprayed onto a host for use in transdermal drug delivery (hereinafter the "preferred transdermal formulation"), a silicone-urea block copolymer is dissolved in a solvent such as isopropanol. Next, except for the propellant, the other ingredients of the composition such a (meth)acrylate PSA, a pharmacologically active agent such as oestradiol or the like, and any optional adjuvants would then be added and dissolved in the isopropyl alcohol with mixing to complete the preferred transdermal formulation. If a propellant is to be included in the fluid composition, it may be added using conventional techniques, e.g., cold filling or pressure filling techniques, after the other ingredients are placed into a suitable spray device.

If desired, the resultant preferred transdermal formulation may be allowed to stand to dissipate air bubbles. When ready to use, the preferred transdermal formulation may be sprayed onto the desired location of the host. Spraying preferably is accomplished using a suitable metered-dose spray on system that controls the dosage, coating thickness, and geometry of the coating. A particularly preferred metered-dose spray on system is described in Assignee's co-pending U.S. patent application filed cocurrently herewith entitled ACTUATOR SYSTEM FOR SPRAYING A FORMULATION ONTO A HOST and having docket No. 54387 USA2A, incorporated herein by reference in its entirety.

The coating should be formed with a suitable thickness that allows the tacky and non-tacky components to undergo the desired phase separation. The skilled worker may select a suitable coating thickness in accordance with conventional practices by giving due consideration to such factors such as the nature of the ingredients used in the fluid composition, the nature of the host, the desired rate of transdermal drug delivery, and the like. For example, in the case of the preferred transdermal formulation, a suitable coating thickness is generally less than about 1000 micrometers, preferably about 250 micrometers to about 750 micrometers, more preferably about 300 to about 600 micrometers.

Once coated, the volatile components of the coated composition, e.g., the volatile solvent, propellant, etc., evaporate. As the volatile components evaporate, separate tacky and non-tacky phases precipitatively form. Due to the nature of the tacky and non-tacky components, the non-tacky phase precipitately forms a protective cover proximal to the top, exposed surface of the covering element. Meanwhile, one or more domains of the tacky phase precipitatively form inside the covering element and proximal to the bottom surface of the covering element proximal and in contact with the host surface. This allows the covering element to remain adhered to the host.

For example, in the case of the preferred transdermal formulation, the isopropyl alcohol and dimethyl ether evaporate relatively quickly after the formulation is coated onto the host. As the coating dries, the silicone-urea block polymer and the (meth)acrylate PSA phase separate to form separate non-tacky and tacky phases, respectively. The siloxane moities of the silicone-urea block copolymer are incompatible with the (meth)acrylate PSA and have a strong tendency to seek the low surface energy surface of the coating. As a result, the silicone-urea block polymer tends to migrate to a low surface energy position at the interface between the covering element and the ambient air. There, the silicone-urea block polymer dries to form a physically crosslinked protective barrier layer, thus providing the covering element with a non-tacky outer surface. In the meantime, the (meth)acrylate PSA precipitates as one or more domains of a tacky phase, at least one of which forms in contact with the host surface. As a result, the covering element derived from the preferred transdermal formulation adheres to the host.

Depending upon the nature of the tacky component, the covering element can be removed from the host by simply pulling the covering element off the host surface without leaving a residue behind. Alternatively, in other embodiments such as those incorporating a (meth)acrylate PSA, the covering element can be removed by swabbing or washing the covering element with a solvent such as isopropyl alcohol to solvate a sufficient amount of the tacky phase to release the element from the host.

Preferably, the degree of tackiness (or non-tackiness) associated with a material can be quantified according to the probe tack test. This test is performed using a digital Polyken Probe Tack Tester, TMI Model 80-02-01 fitted with the "A" annular weight and "F" auxiliary weight accessories. The apparatus is available from Testing Machines, Inc., Amityville, N.Y.

As an overview of the probe tack test, tackiness of a sample is determined by bringing the tip of a flat, circular probe (made from either stainless steel and having a contact surface area of 0.5 $cm^2$ or an aluminum alloy and having a contact area of 0.7 $cm^2$. If both kinds of probes are used to analyse a sample, tack will be given by the value obtained using the stainless steel probe if the two probes yield valves that differ by more than 10% from each other. Otherwise, tack can be the average of the valves obtained from the two probes.) into contact with the material and then measuring the force required to separate the probe from the material. The tackiness is given by this force. More specifically, two patches of the material to be tested are prepared. To make each patch, a sample of the fluid composition is sprayed onto a non-silicone substrate to form a patch over an area of approximately 6.25 $cm^2$ (about 1 $in^2$) so that the coating of material is large enough to cover the opening of the "A" annular weight.

Meanwhile, the Polyken Probe Tack Tester is turned on and allowed to warm up for at least 20 minutes prior to testing. This allows a constant digital display to be achieved. The top surface of the probe and the annular "A" weight are cleaned with methanol. The machine speed is set at 0.5 cm/s and dwell time is set to 2 seconds. The mode switch is set to "track" and the display is zeroed. The mode switch is changed to "peak" after zeroing. The reset button may be pressed if needed in order to re-zero the display.

The "A" weight is positioned over the probe. The patch is placed onto, and should fully cover, the opening of the weight. The patch also should not hang excessively over the edge of the "A" weight in any direction. The combination is then placed into the well of the carrier. The "F" weight is placed on top of the patch with the opening in the "F" weight facing downward. The probe is then caused to contact the surface through the hole in the annular weight.

After the preset dwell time, a carriage rises at the preset speed to pull the weight/patch combination away from the probe. The peak force required to separate the probe from the surface is measured in units of "grams of tack". The other patch sample is then tested in the same way. The tackiness is given by the average of the two measurements. According to this preferred technique for measuring tackiness, a material is considered to be tacky for purposes of the present invention if the material is characterized by more than 10, preferably about 25 or more, grams of tack. On the other hand, a material will be considered to be non-tacky if the material is characterized by 10 or less, preferably about 5 or less, more preferably 0, grams of tack.

The present invention will now be further described with reference to the following examples.

Preparation of Non-Tacky Components in Accordance with the Present Invention

1. Non-Tacky Component 1 (NTC1)

Under a nitrogen atmosphere, 4.34 g of isophorone diisocyanate (IPDI, available from Bayer Corporation, Pittsburgh, Pa.) was slowly added with stirring to a solution of 4.50 g of polydimethylsiloxane diamine with a number average molecular weight of 5400 (PDMS, prepared in accordance with the method for making "Polydimethylsiloxane Diamine A" found in WO 96-34029), 12.38 g of polypropylene oxide diamine with a number average molecular weight of 2000 (PPO, available as Jeffamine® D2000 from Huntsman Corporation, Austin, Tex.), and 1.28 g of 1,3-diaminopentane (DAMP, available as DYTEK EP from E.I. DuPont de Nemours & Co., Wilmington, Del.) in 127.50 g of isopropyl alcohol (IPA). The reaction mixture was stirred for 30 minutes. This provided a 15% by weight solution of the NTC in IPA. The polymer contained 20% by weight PDMS, 25% by weight DAMP/IPDI, and 55% by weight PPO.

2. Non-Tacky Component 2 (NTC2)

Using the same general method and the same monomers as above but varying the amount of monomer, a 15% by weight solution of the NTC in IPA was prepared. The polymer contained 20% by weight PDMS, 30% by weight DAMP/IPDI, and 55% by weight PPO.

3. Non-Tacky Component (NTC3)

Using same general method and monomers of NTC1 except that Jeffamine D400 was used instead of Jeffamine D2000, a 15% by weight solution of the NTC in IPA was prepared. The polymer contained 20% by weight PDMS, 25% by weight DAMP/IPDI, and 55% by weight PPO.

4. Preparation of "Dried" Non-Tacky Component

Dried non-tacky component, i.e., NTC1, NTC2 or NTC3, is prepared by spreading a portion of the non-tacky component solution onto a fluoropolymer coated release liner (1022 Scotchpak™ from Minnesota Mining & Manufacturing Company, St. Paul, Minn.). The coated liner is then allowed to dry at ambient conditions. The resulting dried non-tacky component is stripped from the release liner and stored in a glass container.

Preparation of Tacky Components

The tacky component used in the examples below are prepared generally according to the methods described below. The inherent viscosity values which are reported were measured by conventional means using a Canon-Fenske #50 viscometer in a water bath controlled at 27° C. to measure the flow of 10 milliliters of a polymer solution. The test procedure used and the apparatus used are described in detail in "Textbook of Polymer Science", F. W. Billmeyer, Wiley Interscience, Second Edition, 1971, Pages 84 and 85.

1. Isooctyl Acrylate/Acrylamide/Vinyl Acetate (75/5/20) (TC1)

A 1 quart (0.95 liter) amber glass bottle was charged with 96.75 g of isooctyl acrylate, 6.45 g of acrylamide, 25.8 g of vinyl acetate, 0.129 g of 2,2'-azobis(2,4-dimethylpentanenitrile), 464.4 g of ethyl acetate and 51.6 g of methanol. The bottle was purged for 2 minutes with nitrogen at a flow rate of 1 liter per minute. The bottle was sealed and placed in a rotating water bath at 45° C. for 24 hours. The bottle was removed from the water bath, opened, and then charged with 0.129 g of 2,2'-azobis(2,4-dimethylpentanenitrile). The bottle was purged for 2 minutes with nitrogen at a flow rate of 1 liter per minute. The bottle was sealed and placed in a rotating water bath at 45° C. for an additional 24 hours. The tacky component, TC1, had a measured inherent viscosity of 0.7 deciliter/g in ethyl acetate at a concentration of 0.15 g/deciliter.

2. Isooctyl Acrylate/Acrylamide/Vinyl Acetate (75/5/20) (TC2)

A tacky component, TC2, was made using the procedure to prepare TC1 except that the amount of solvent used was adjusted to provide an inherent viscosity of 1.2 deciliters/g in ethyl acetate.

3. Preparation of "Dried" Tacky Component

Dried tacky component, i.e., either TC1 or TC2, is prepared by coating a solution of the tacky component onto a release liner. The coated liner is oven dried (e.g. 4 minutes at 43° C., 2 minutes at 85° C., and 10 minutes at 149° C.) to remove the solvents and reduce the level of residual monomers. The dried tacky component is stripped off the release liner and stored in a glass container.

EXAMPLE 1

A 0.0132 g portion of dried NTC2, 0.2495 g of dried TC2, and 1.1410 g of isopropyl alcohol (IPA) were placed in a 10 cc plastic coated glass vial. A continuous valve equipped with a solution gasket (The gasket was made from FLEXOMER™ 1085 polyolefin, available from Union Carbide, Danbury Conn.) was crimped onto the vial. Dimethyl ether (DME, 3.6273 g) was added to the vial through the valve stem. The vial was placed on a roller and allowed to mix. A clear solution was obtained. The specific formulations of the resulting fluid compositions (% weight/weight) are shown in Table 1, below.

The fluid composition was dispensed through a vertical actuator attached to a funnel shaped spacer onto microporous polyethylene film (CoTran™ 9710 from Minnesota Mining & Manufacturing, St. Paul, Minn.). The funnel was selected to provide test covering elements having a 5 cm² surface area. The covering elements were allowed to dry at ambient conditions.

The surface tack of the dried covering elements was measured using the test method described above except that a stainless steel probe was used.

EXAMPLES 2–13

Using the general method of Example 1, a series of fluid compositions was prepared and tested in which the amount and type of NTC and the amount of IPA were varied from composition to composition. The specific formulations of the fluid compositions (% weight/weight) are shown in Table 1, below. The fluid compositions of Examples 1–7 were prepared with NTC1; those of Examples 8–14 were prepared with NTC2. The fluid compositions of Examples 1, 2, 3, and 8 through 14 were clear solutions. The fluid compositions of Examples 4 through 7 contained a precipitate. The fluid compositions were shaken vigorously just prior to being dispensed. The tack values are given in Table 1 below where each value is the average of duplicate runs.

TABLE 1

| Fluid composition | NTC | TC | IPA | DME | Tack (g) |
|---|---|---|---|---|---|
| 1 | 0.3 | 5.0 | 22.7 | 72.0 | 0 |
| 2 | 0.4 | 5.0 | 26.7 | 67.9 | 0 |
| 3 | 0.8 | 5.0 | 26.9 | 67.3 | 0 |
| 4 | 1.0 | 5.0 | 21.8 | 72.2 | 0 |
| 5 | 0.8 | 5.0 | 16.1 | 78.1 | 0 |

TABLE 1-continued

| Fluid composition | NTC | TC | IPA | DME | Tack (g) |
|---|---|---|---|---|---|
| 6 | 0.4 | 5.0 | 16.1 | 78.5 | 0 |
| 7 | 0.6 | 5.1 | 21.8 | 72.5 | 0 |
| 8 | 0.2 | 5.0 | 22.0 | 72.8 | 0 |
| 9 | 0.4 | 5.0 | 26.5 | 68.1 | 0 |
| 10 | 0.8 | 5.0 | 26.7 | 67.5 | 0 |
| 11 | 1.1 | 5.1 | 21.7 | 72.1 | 0 |
| 12 | 0.8 | 4.9 | 16.0 | 78.3 | 0 |
| 13 | 0.4 | 5.0 | 16.2 | 78.4 | 0 |
| 14 | 0.6 | 5.0 | 21.8 | 72.6 | 0 |

EXAMPLE 15

A solution containing 6.2 percent by weight of NTC2 in IPA was prepared by diluting 0.5020 g of a 15% by weight solution of NTC2 in IPA with 7.5338 g of IPA. A 0.5118 g portion of the 6.2% solution and 0.2532 g of dried TC2 were placed in a 10 cc plastic coated glass vial. A continuous valve equipped with a solution gasket (The gasket was made from FLEXOMER™ 1085 polyolefin, available from Union Carbide, Danbury, Conn.) was crimped onto the vial. Dimethyl ether (DME, 4.2451 g) was added to the vial through the valve stem. The vial was placed on a roller and allowed to mix. The specific formulations of the resulting fluid compositions (% weight/weight) are shown in Table 2, below.

The fluid compositions were dispensed through a vertical actuator attached to a funnel shaped spacer onto microporous polyethylene film (CoTran™ 9710, Minnesota Mining & Manufacturing, St. Paul, Minn.). The funnel was selected to provide test covering elements having a 5 cm² surface area. The covering elements were allowed to dry at ambient conditions.

The surface tack of the dried covering elements was measured using the test method described above except that a stainless steel probe was used.

EXAMPLES 16–32

Using the general method of Example 15, a series of fluid compositions in which the amount and type of NTC and the amount of IPA were varied was prepared and tested. The specific formulations of the fluid compositions (% weight/weight) are shown in Table 2, below. The fluid compositions of Examples 15–23 were prepared with NTC2; those of Examples 24–32 were prepared with NTC3. In all fluid compositions the tacky component was TC2. The fluid compositions of Examples 17, 20 and 32 were clear solutions; those of Examples 23, 24, 25, 26 and 29 were hazy solutions; and the remaining fluid compositions contained a precipitate. The control composition (no NTC) was a clear solution. The fluid compositions were shaken vigorously prior to being dispensed. The tack values are given in Table 2 below where each value is the average of duplicate runs.

TABLE 2

| Fluid compositions | NTC | TC | IPA | DME | Tack(g) |
|---|---|---|---|---|---|
| Control | 0 | 5.2 | 20.8 | 74.0 | 69 |
| 15 | 0.09 | 5.1 | 10.1 | 84.71 | 26 |
| 16 | 0.2 | 5.0 | 20.3 | 74.5 | 13 |
| 17 | 0.3 | 5.0 | 29.8 | 64.9 | 0 |

TABLE 2-continued

| Fluid compositions | NTC | TC | IPA | DME | Tack(g) |
|---|---|---|---|---|---|
| 18 | 0.3 | 5.0 | 10.7 | 84.0 | 0 |
| 19 | 0.5 | 5.1 | 19.7 | 74.7 | 0 |
| 20 | 0.8 | 5.1 | 29.8 | 64.3 | 0 |
| 21 | 0.4 | 5.1 | 10.2 | 84.3 | 0 |
| 22 | 0.8 | 5.0 | 20.7 | 73.5 | 0 |
| 23 | 1.1 | 5.0 | 28.9 | 65.0 | 0 |
| 24 | 0.1 | 5.0 | 10.3 | 84.6 | 32 |
| 25 | 0.2 | 5.0 | 19.9 | 74.9 | 0 |
| 26 | 0.3 | 5.1 | 30.1 | 64.5 | 30 |
| 27 | 0.3 | 5.0 | 10.6 | 84.1 | 14 |
| 28 | 0.5 | 5.0 | 19.4 | 75.1 | 0 |
| 29 | 0.8 | 5.0 | 29.4 | 64.8 | 0 |
| 30 | 0.4 | 5.1 | 10.0 | 84.5 | 0 |
| 31 | 0.8 | 5.1 | 19.6 | 74.5 | 0 |
| 32 | 1.1 | 5.0 | 29.0 | 64.9 | 0 |

EXAMPLES 33–50

Using the general method of Example 15, a series of fluid compositions in which the amount and type of NTC and the amount of IPA were varied was prepared and tested. The specific formulations of the fluid compositions (% weight/weight) are shown in Table 3, below. The fluid compositions of Examples 33–41 were prepared with NTC2; those of Examples 42–50 were prepared with NTC3. In all fluid compositions the tacky component was TC1. The fluid compositions of Examples 41, 42, 43, 44, 47 and 50 were clear solutions; the remaining fluid compositions contained a precipitate. The control composition (no NTC) was a clear solution. The fluid compositions were shaken vigorously prior to being dispensed. The tack values are given in Table 3 below where each value is the average of duplicate runs.

TABLE 3

| Fluid compositions | NTC | TC | IPA | DME | Tack(g) |
|---|---|---|---|---|---|
| Control | 0 | 10.4 | 20.0 | 69.6 | 86 |
| 33 | 0.09 | 10.1 | 10.0 | 79.81 | 47 |
| 34 | 0.2 | 10.2 | 19.9 | 69.7 | 38 |
| 35 | 0.3 | 10.0 | 29.7 | 60.0 | 39 |
| 36 | 0.3 | 10.0 | 9.9 | 79.8 | 27 |
| 37 | 0.5 | 10.1 | 19.8 | 69.6 | 19 |
| 38 | 0.8 | 10.1 | 29.7 | 59.4 | 25 |
| 39 | 0.4 | 9.9 | 9.9 | 79.8 | 32 |
| 40 | 0.8 | 10.0 | 19.2 | 70.0 | 13 |
| 41 | 1.1 | 10.0 | 29.1 | 59.8 | 0 |
| 42 | 0.1 | 10.1 | 10.2 | 79.6 | 49 |
| 43 | 0.2 | 10.0 | 19.9 | 69.9 | 28 |
| 44 | 0.3 | 10.0 | 29.9 | 59.8 | 28 |
| 45 | 0.3 | 9.9 | 11.6 | 78.2 | 14 |
| 46 | 0.5 | 10.0 | 20.1 | 69.4 | 0 |
| 47 | 0.7 | 10.0 | 29.2 | 60.1 | 0 |
| 48 | 0.4 | 10.1 | 9.6 | 79.9 | 0 |
| 49 | 0.8 | 10.3 | 20.0 | 68.9 | 0 |
| 50 | 1.1 | 9.9 | 28.3 | 60.7 | 0 |

EXAMPLES 51–58

Using the general method of Example 15, a series of fluid compositions in which the amount of IPA was varied was prepared and tested. The specific formulations of the fluid compositions (% weight/weight) are shown in Table 4, below. All fluid compositions were prepared with NTC2. In all fluid compositions the tacky component was TC2. The fluid compositions of Examples 55, 56, 57 and 58 were clear solutions; the fluid composition of Example 51 was a hazy solution; and the remaining fluid compositions contained a precipitate. The control composition (no NTC) was a clear solution. The fluid compositions were shaken vigorously prior to being dispensed. The tack values are given in Table 4 below where each value is the average of duplicate runs.

TABLE 4

| Fluid compositions | NTC | TC | IPA | DME | Tack(g) |
|---|---|---|---|---|---|
| Control | 0 | 5.0 | 20.2 | 74.8 | 52 |
| 51 | 1.9 | 2.9 | 20.9 | 74.3 | 0 |
| 52 | 1.8 | 3.1 | 18.6 | 76.5 | 0 |
| 53 | 1.8 | 3.1 | 16.4 | 78.7 | 0 |
| 54 | 1.8 | 3.1 | 15.0 | 80.0 | 0 |
| 55 | 1.8 | 3.0 | 24.1 | 71.0 | 0 |
| 56 | 1.8 | 3.0 | 28.5 | 66.6 | 0 |
| 57 | 1.8 | 3.2 | 34.5 | 60.5 | 0 |
| 58 | 1.8 | 3.1 | 42.6 | 52.6 | 0 |

EXAMPLE 59

A 0.0112 g portion of dried NTC2, 0.2517 g of TC2, 0.1105 g of ethyl oleate (EO) and 1.0660 g of isopropyl alcohol (IPA) were placed in a 10 cc plastic coated glass vial. A continuous valve equipped with a solution gasket (The gasket was made from FLEXOMER™ 1085 polyolefin, available from Union Carbide, Danbury, Conn.) was crimped onto the vial. Dimethyl ether (DME, 3.6331 g) was added to the vial through the valve stem. The vial was placed on a roller and allowed to mix. A clear solution was obtained. The specific formulation of the fluid composition (% weight/weight) is shown in Table 5 below.

The fluid composition was dispensed through a vertical actuator attached to a funnel spaced spacer onto microporous polyethylene film (CoTran™ 9710 from 3M Company). The funnel was selected to provide test covering elements having a 5 cm² surface area. The covering elements were allowed to dry at ambient conditions.

The surface tack of the dried covering elements was measured using the test method described above except that a stainless steel probe was used.

EXAMPLES 60–72

Using the general method of Example 59, a series of fluid compositions in which the amount and type of NTC, and the amount of IPA were varied was prepared and tested. The the specific formulations of the fluid compositions (% weight/weight) are shown in Table 5, below. The fluid compositions of Examples 60–65 were prepared with NTC2; those of Examples 66–72 were prepared using NTC1. In all fluid compositions the tacky component was TC2. The fluid compositions of Examples 59, 60, 61, 66–69, 71 and 72 were clear solutions; the remaining fluid compositions contained a precipitate. The fluid compositions were shaken vigorously prior to being dispensed. The tack values are given in Table 5 below where each value is the average of duplicate runs.

TABLE 5

| Fluid composition | NTC | TC | EO | IPA | DME | Tack (g) |
|---|---|---|---|---|---|---|
| 59 | 0.2 | 5.0 | 2.2 | 21.0 | 71.6 | 23 |
| 60 | 0.4 | 5.1 | 2.3 | 26.0 | 66.2 | 15 |
| 61 | 0.8 | 4.9 | 2.0 | 26.1 | 66.2 | 11 |

TABLE 5-continued

| Fluid composition | NTC | TC | EO | IPA | DME | Tack (g) |
|---|---|---|---|---|---|---|
| 62 | 1.0 | 5.1 | 2.1 | 20.7 | 71.1 | 12 |
| 63 | 0.8 | 5.0 | 2.2 | 15.5 | 76.5 | 11 |
| 64 | 0.5 | 5.0 | 2.0 | 15.4 | 77.1 | 24 |
| 65 | 0.6 | 5.0 | 2.0 | 20.7 | 71.7 | 0 |
| 66 | 0.2 | 4.9 | 2.2 | 21.3 | 71.4 | 15 |
| 67 | 0.4 | 5.1 | 2.1 | 26.1 | 66.3 | 13 |
| 68 | 0.8 | 5.1 | 2.1 | 26.2 | 65.8 | 12 |
| 69 | 1.1 | 5.0 | 2.0 | 20.9 | 71.0 | 0 |
| 70 | 0.8 | 5.0 | 2.1 | 15.6 | 76.5 | 0 |
| 71 | 0.4 | 5.0 | 2.2 | 15.5 | 76.9 | 16 |
| 72 | 0.6 | 5.0 | 2.1 | 20.7 | 71.6 | 25 |

EXAMPLES 73–81

Using the general method of Example 59, a series of fluid compositions in which the amounts of NTC and IPA were varied was prepared and tested. The specific formulations of the fluid compositions (% weight/weight) are shown in Table 6, below. All fluid compositions were prepared with NTC1 and TC2. The fluid compositions of Examples 73 and 75 were clear solutions; the remaining fluid compositions phase separated on standing. The control composition (no NTC) was a clear solution. The fluid compositions were shaken vigorously prior to being dispensed. The tack values were measured using an aluminum probe according to the test method described above and are given in Table 6 below where each value is the average of duplicate runs.

TABLE 6

| Fluid composition | NTC | TC | EO | IPA | DME | Tack (g) |
|---|---|---|---|---|---|---|
| Control | 0 | 5.0 | 2.2 | 25.6 | 67.2 | 97 |
| 73 | 3.1 | 5.1 | 2.2 | 25.0 | 64.6 | 12 |
| 74 | 4.0 | 5.0 | 2.2 | 20.3 | 68.5 | 0 |
| 75 | 4.0 | 5.4 | 2.3 | 30.4 | 58.3 | 0 |
| 76 | 5.0 | 5.1 | 2.2 | 15.0 | 72.7 | 0 |
| 77 | 5.0 | 5.0 | 2.3 | 25.1 | 62.6 | 0 |
| 78 | 5.0 | 5.1 | 2.2 | 34.7 | 53.0 | 0 |
| 79 | 6.0 | 5.0 | 2.2 | 19.6 | 67.2 | 0 |
| 80 | 6.0 | 5.0 | 2.4 | 29.9 | 56.7 | 0 |
| 81 | 7.0 | 5.0 | 2.4 | 24.8 | 60.8 | 0 |

The fluid compositions of Examples 73 through 81 and the control composition were dispensed through a vertical actuator attached to a funnel shaped spacer onto a Teflon® coated woven liner. The funnel was selected to provide test covering elements having a 5 cm² surface area. The covering elements were allowed to dry at ambient conditions. The tack of the air exposed surface was measured according to the test method described above using an aluminum probe. After the tack of the air exposed surface had been measured, the covering element was peeled off of the liner. The surface that had originally been exposed to the air was attached to a polyethylene backing using double sided tape. The tack of the substratum surface, i.e., the surface that was originally against the liner, was then measured using the same method. The tack measurements are shown in Table 7 below where each value is the average of duplicate runs.

TABLE 7

| Fluid composition | Air Exposed Surface Tack (g) | Substratum Surface Tack (g) |
|---|---|---|
| Control | 117 | 125 |
| 73 | 28 | 87 |
| 74 | 0 | 35 |
| 75 | 0 | 15 |
| 76 | 0 | 80 |
| 77 | 0 | 14 |
| 78 | 0 | 29 |
| 79 | 0 | 63 |
| 80 | 0 | 12 |
| 81 | 0 | 37 |

EXAMPLE 82

A transdermal drug delivery system in accordance with the present invention was prepared and tested in the following manner. A 0.1165 g portion of estradiol, 0.2429 g of isopropyl myristate, 0.1202 g of glyceryl monolaurate, 0.4920 g of ethyl oleate, 2.5309 g of TC2 1.9955 g of dried NTC1, and 12.5714 g of isopropyl alcohol were placed in a 4 ounce (118 ml) plastic coated glass vial. A continuous valve equipped with a solution gasket (The gasket was made from FLEXOMER™ 1085 polyolefin, available from Union Carbide, Danbury, Conn.) was crimped onto the vial. Dimethyl ether (32.162 g) was added to the vial through the valve stem. The vial was placed on a roller and allowed to mix until a solution was obtained. The vial was chilled in dry ice for about 10 minutes. The continuous valve was removed and replaced with a 100 µL metered dose valve (Spraymiser™ M3654, Minnesota Mining & Manufacturing, St. Paul, Minn.) equipped with a gasket made from FLEXOMER™ 1085 polyolefin. The vial was allowed to equilibrate to ambient temperature.

Human cadaver skin was mounted in a 2 cm² Franz diffusion cell. The fluid composition was dispensed through a vertical actuator and a funnel spacer onto the skin. Dispensed volumes ranged from 400 to 1000 µL. It was observed that some of the fluid composition adhered to the cell cap and was not on the skin. The covering elements were allowed to dry. Receptor solution (30% N-methyl-2-pyrrolidone in water) was added to the cell. The cells were placed in constant temperature (32° C.) and humidity (40% relative humidity) chamber. Samples of the receptor solution were withdrawn at 12, 24, and 48 hours and analyzed for estradiol content using high performance liquid chromatography (Supelcosil™ LC-18 column, 150×4.6 mm, 5 µm particle size (available from Supelco); mobile phase: water/acetonitrile (60/40 v/v); flow rate at 2 ml/min; detector UV at 280 nm at 0.2 AUFS; run time of 6 minutes; injection volume of 20 µL). The results are shown in Table 8 below where each value is the average obtained from four independent determinations.

TABLE 8

| Fluid composition | Average Cumulative Estradiol Penetrating ($\mu g/cm^2$) | | |
|---|---|---|---|
| Volume | 12 hours | 24 hours | 48 hours |
| 400 µL | 1.8 | 3.4 | 5.1 |
| 600 µL | 1.6 | 2.5 | 3.5 |
| 800 µL | 1.8 | 3.9 | 6.9 |
| 1000 µL | 2.2 | 4.3 | 7.0 |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A fluid composition suitable for in situ forming and adhering a touch-dry, non-tacky covering element onto a surface, comprising:
   (a) an effective amount of a tacky component such that the formed covering element adheres to the surface, wherein the tacky component comprises a pressure sensitive adhesive comprising a (meth)acrylate polymer, further wherein the (meth)acrylate polymer is a copolymer of monomers comprising about 40 to about 100 weight percent of an alkyl (meth)acrylate and 0 to about 60 weight percent of a free radically copolymerizable monomer;
   (b) a film-forming, non-tacky component, wherein said film-forming; non-tacky component comprises at least one low surface energy, surface seeking moiety, wherein said film-forming, non-tacky component is incompatible with the tacky component, and wherein the film-forming, non-tacky component is present in an effective amount such that upon application it undergoes phase separation from the tacky component such that an outer surface of the in situ formed covering element is non-tacky when the covering element is touch dry; and
   (c) a sufficient amount of at least one volatile solvent such that the fluid composition has a coatable viscosity allowing the fluid composition to be coated onto said surface.

2. The fluid composition of claim 1, wherein the alkyl (meth)acrylate comprises an alkyl moiety of 1 to 10 carbon atoms and the copolymerizable monomer comprises a functional group selected from carboxylic acid, carboxylic acid ester, hydroxyl, anhydride, epoxy, thiol, isocyanate, sulfonamide, urea, carbamate, carboxamide, amine, ammonium, oxy, oxo, nitro, nitrogen, sulfur, phosphate, phosphonate, cyano, and combinations thereof.

3. The fluid composition of claim 1, wherein the tacky component comprising a copolymer derived from monomers comprising, based upon the total weight of the monomers, 40 to 100 weight percent of isooctyl (meth)acrylate, 0 to 60 weight percent of(meth)acrylamide, and 0 to 30 weight percent of vinyl acetate.

4. A fluid composition suitable for in situ forming and adhering a touch-dry, non-tacky covering element onto a surface, comprising:
   (a) an effective amount of a tacky component such that the formed covering element adheres to the surface, wherein the weight ratio of the tacky component to the non-tacky component is in the range from about 1:10 to about 10:1,
   (b) a film-forming, non-tacky component, wherein said film-forming, non-tacky component comprises at least one low surface energy, surface seeking moiety, wherein said film-forming, non-tacky component is incompatible with the tacky component, and wherein the film-forming, non-tacky component is present in an effective amount such that upon application it undergoes phase separation from the tacky component such that an outer surface of the in situ formed covering element is non-tacky when the covering element is touch dry; and
   (c) a sufficient amount of at least one volatile solvent such that the fluid composition has a coatable viscosity allowing the fluid composition to be coated onto said surface.

5. A fluid composition suitable for in situ forming and adhering a touch-dry, non-tacky covering element onto a surface comprising:
   (a) an effective amount of a tacky component such that the formed covering element adheres to the surface;
   (b) a film-forming, non-tacky component, wherein said film-forming, non-tacky component comprises at least one low surface energy, surface seeking moiety, wherein said film-forming, non-tacky component is incompatible with the tacky component, and wherein the film-forming, non-tacky component is present in an effective amount such that upon application it undergoes phase separation from the tacky component such that an outer surface of the in situ formed covering element is non-tacky when the covering element is touch dry; and
   (c) a sufficient amount of at least one volatile solvent such that the fluid composition has a coatable viscosity allowing the fluid composition to be coated onto said surface, wherein the volatile solvent comprises isopropanol.

6. A fluid composition suitable for in situ forming and adhering a touch- dry, non-tacky covering element onto a surface comprising:
   (a) from about 1 to about 50 weight percent tacky component, wherein the tacky component comprises a pressures sensitive adhesive comprising a copolymer of monomers comprising about 40 to about 100 weight percent alkyl (meth)acrylate and 0 to about 60 weight percent of a free radically copolymerizable monomer coating a fluid composition onto a surface, wherein the composition comprises;
   (b) a film-forming, non-tacky component, wherein said film-forming, non-tacky component comprises at least one low surface energy, surface seeking moiety, wherein said film-forming, non-tacky component is incompatible with the tacky component, and wherein the film-forming, non-tacky component is present in an effective amount such that an outer surface of the in situ formed covering element is non-tacky when the covering element is touch dry, and wherein the weight ratio of the tacky phase to the non-tacky phase is in the range from 1:20 to 20:1; and
   (c) a sufficient amount of at least one volatile solvent such that the fluid composition has a coatable viscosity allowing the fluid composition to be coated onto said surface.

7. A fluid composition suitable for in situ forming and adhering a touch-dry, non-tacky covering element onto a surface, comprising:
   (a) an effective amount of a tacky component such that the formed covering element adheres to the surface;
   (b) a film-forming, non-tacky component, wherein said film-forming, non-tacky component comprises at least one low surface energy, surface seeking moiety, wherein said film-forming, non-tacky component is incompatible with the tacky component, and wherein the film-forming, non-tacky component is present in an effective amount such that upon application it undergoes phase separation from the tacky component such that an outer surface of the in situ formed covering element is non-tacky when the covering element is touch dry, further wherein the film-forming, non-tacky component comprises a polymer comprising at least one siloxane moiety and/or at least one fluorine containing mole; and (c) a sufficient amount of at least one volatile solvent such that the fluid composition has a coatable viscosity allowing the fluid composition to be coated onto said surface.

8. A fluid composition suitable for in situ forming and adhering a touch-dry, non-tacky covering element onto a surface, comprising:

(a) an effective amount of a tacky component such that the formed covering element adheres to the surface, wherein the tacky component comprises an acrylate pressure sensitive adhesive comprising a copolymer formed by copolymerizing about 60 to about 80 percent isooctyl acrylate about 1 to about 10 percent acrylamide, and about 5 to about 30 percent vinyl acetate;

(b) a film-forming, non-tacky component, wherein said film-forming non-tacky component comprises at least one low surface energy, surface seeking moiety, wherein said film-forming, non-tacky component is incompatible with the tacky component, and wherein die film-forming, non-tacky component is present in an effective amount such that upon application it undergoes phase separation from the tacky component such that an outer surface of the in situ formed covering element is non-tacky when the covering element is touch dry and (c) a sufficient amount of at least one volatile solvent such that the fluid composition has a coatable viscosity allowing the fluid composition to be coated onto said surface.

9. A fluid composition as in claim 4, 5, 6, or 7 in which the tacky component comprising a pressure sensitive adhesive comprising a (meth)acrylate polymer.

10. A fluid composition as in claim 1, 4, 5, or 6 in which the film-forming, non-tacky component comprises a polymer selected from the group consisting of a cellulosic polymer, a siloxane containing polymer, a polyvinylacetate, a polymethyl(meth)acrylate, a fluorinated polymer, a fluorosilicone polymer, a styrene-butadiene rubber, a polyurethane, a vinyl copolymer, a polyolefin, a polyamide, a polyimide, a polyamidemeide, a polyester, and combinations of these.

11. A fluid composition as in claim 1, 4, 6, or 7 in which the volatile solvent is selected from the group consisting of ethanol, acetone, isopropanol, or a combination thereof.

12. A fluid composition as in claim 1, 4, 5, 6, or 7 further comprising a therapeutically effective amount of a pharmacologically active agent.

* * * * *

UNITED STATES PATENT AND TRADEMARK OFFICE
CERTIFICATE OF CORRECTION

PATENT NO. : 6,958,154 B2
APPLICATION NO. : 10/619008
DATED : October 25, 2005
INVENTOR(S) : Patricia J. A. Brandt It is certified that error appears in the above-identified patent and that said Letters Patent is hereby corrected as shown below:

<u>Title Page, Item [56]</u>
References Cited, under U.S. Patent Documents, please delete:
"6,627,216 B2   9/2003 Wirtanen et al........424/443" and insert in place thereof:
--6,627,216 B2...9/2003 Brandt et al.   424/443.--

<u>Column 8,</u>
Line 24, delete "anydride," and insert in place thereof --anhydride,--.
Line 27, delete "phosponante" and insert in place thereof --phosphonate--.

<u>Column 12,</u>
Line 7, delete "poloysiloxane" and insert in place thereof --polysiloxane--.
Line 33, delete the third occurrence of "about".

<u>Column 13,</u>
Line 13, delete the second occurrence of "about".

<u>Column 14,</u>
Line 10, delete "polydimethysiloxane" and insert in place thereof --polydimethylsiloxane--.

<u>Column 15,</u>
Line 33, delete "dimethoxcymethane" and insert in place thereof --dimethoxymethane--.

<u>Column 17,</u>
Line 63, delete "hyperuricaemia" and insert in place thereof --hyperuricaernia--.

<u>Column 21,</u>
Line 21, delete "ester" and insert in place thereof --esters--.
Line 24, delete "(N,N dimethylamino)" and insert in place thereof --(N,N-dimethylamino)--.

<u>Column 23,</u>
Line 26, delete "valves" and insert in place thereof --values--.
Line 28, delete "valves" and insert in place thereof --values--.

<u>Column 28,</u>
Line 34, delete "spaced" and insert in place thereof --shaped--.
Line 47, delete "was" and insert in place thereof --as--.
Line 47, delete "The the" and insert in place thereof --The--.

UNITED STATES PATENT AND TRADEMARK OFFICE
CERTIFICATE OF CORRECTION

PATENT NO. : 6,958,154 B2
APPLICATION NO. : 10/619008
DATED : October 25, 2005
INVENTOR(S) : Patricia J. A. Brandt It is certified that error appears in the above-identified patent and that said Letters Patent is hereby corrected as shown below:

<u>Column 31,</u>
Claim 1, Line 23, delete "film-forming;" and insert in place thereof --film-forming,--.

<u>Column 32,</u>
Claim 5, Line 10, delete "surface" and insert in place thereof --surface,--.

<u>Column 33,</u>
Claim 7, Line 7, delete "mole" and insert in place thereof --moiety--.
Claim 8, Line 20, delete "acrylate" and insert in place thereof --acrylate,--
Claim 8, Line 24, delete "film-forming" and insert in place thereof --film-forming,--.
Claim 8, Line 28, delete "die" and insert in place thereof --the <u>Column 34,</u>
Claim 8, Line 4, delete "dry" and insert in place thereof --dry;--.
Claim 9, Line 10, delete "claim" and insert in place thereof --claims--.
Claim 10, Line 13, delete "claim" and insert in place thereof --claims--.
Claim 10, Line 20, delete "polyamidemeide" and insert in place thereof --polyamideimide--.
Claim 11, Line 22, delete "claim" and insert in place thereof --claims--.
Claim 12, Line 25, delete "claim" and insert in place thereof --claims--.

Signed and Sealed this

Third Day of April, 2007

JON W. DUDAS
*Director of the United States Patent and Trademark Office*